(12) United States Patent
Fitzpatrick

(10) Patent No.: US 12,227,486 B1
(45) Date of Patent: Feb. 18, 2025

(54) SYSTEMS AND METHODS FOR THE PRODUCTION OF LEVULINIC ACID, FURFURAL, AND FORMIC ACID

(71) Applicant: Biofine Technology LLC, Brookline, MA (US)

(72) Inventor: Stephen W. Fitzpatrick, Framingham, MA (US)

(73) Assignee: Biofine Technology, LLC, Brookline, MA (US)

( * ) Notice: Subject to any disclaimer, the term of this patent is extended or adjusted under 35 U.S.C. 154(b) by 0 days.

(21) Appl. No.: 18/787,536

(22) Filed: Jul. 29, 2024

(51) Int. Cl.
*C07D 307/50* (2006.01)
*C07C 51/00* (2006.01)

(52) U.S. Cl.
CPC ............ *C07D 307/50* (2013.01); *C07C 51/00* (2013.01)

(58) Field of Classification Search
CPC .................................................... C07D 307/50
See application file for complete search history.

(56) References Cited

U.S. PATENT DOCUMENTS

| | | | |
|---|---|---|---|
| 4,897,497 A | 1/1990 | Fitzpatrick | |
| 5,608,105 A | 3/1997 | Fitzpatrick | |
| 8,138,371 B2 | 3/2012 | Fitzpatrick | |
| 8,765,998 B2 | 7/2014 | Fitzpatrick | |
| 9,481,626 B2 | 11/2016 | Fitzpatrick | |
| 9,884,834 B2 | 2/2018 | Pasanen | |

FOREIGN PATENT DOCUMENTS

IN 513998 11/2022

OTHER PUBLICATIONS

Weingarten, Energy Environ. Sci., 2012, 5, 7559.*
Luo, Catalysis Today 319 (2019) 14-24.*
Hayes et al., "The biofine process—production of levulinic acid, furfural, and formic acid from lignocellulosic feedstocks," Biorefineries—Industrial Processes and Product, Apr. 21, 2006, 1:139-64, 21 pages.
Luo et al., "The production of furfural directly from hemicellulose in lignocellulosic biomass: A review," Catalysis Today, Jul. 5, 2018, 319:14-24, 41 pages.
Weingarten et al., "Production of levulinic acid from cellulose by hydrothermal decomposition combined with aqueous phase dehydration with a solid acid catalyst," Energy & Environmental Science, Apr. 19, 2012, 5(6):7559-74, 1 page (abstract only).

* cited by examiner

*Primary Examiner* — Nizal S Chandrakumar
(74) *Attorney, Agent, or Firm* — Fish & Richardson P.C.

(57) ABSTRACT

The disclosure relates to systems and methods for the production of levulinic acid, furfural, and formic acid from feedstock materials containing cellulose and hemicellulose. The levulinic acid, furfural, and formic acid can each be produced in relatively high yield simultaneously and in the same reactor vessel.

12 Claims, 3 Drawing Sheets

SYSTEMS AND METHODS FOR THE PRODUCTION OF LEVULINIC ACID, FURFURAL, AND FORMIC ACID

FIELD

The disclosure relates to systems and methods for the production of levulinic acid, furfural, and formic acid from feedstock materials containing cellulose and hemicellulose. The levulinic acid, furfural, and formic acid can each be produced in relatively high yields simultaneously and in the same reactor vessel.

BACKGROUND

Cellulosic feedstocks can be converted into biofuels, commodity chemicals, carbonaceous biochar and/or sequestered carbon.

SUMMARY

The disclosure relates to systems and methods for the production of levulinic acid, furfural, and formic acid from feedstock materials containing cellulose and hemicellulose. The levulinic acid, furfural, and formic acid can each be produced in relatively high yields simultaneously and in the same reactor vessel.

The systems and methods allow for the production of levulinic acid, furfural, and formic acid in a relatively energy-efficient manner, with relatively little carbon dioxide emissions and/or in a relatively scalable manner. The production of levulinic acid, furfural, and formic acid can be performed simultaneously in a single reaction vessel, with a relatively short residence time and relatively steady controlled reaction conditions, thereby providing relatively high yields of levulinic acid, furfural, and formic acid, and/or reducing operational and/or production costs. The systems and methods allow for relatively easy scale up for the production of levulinic acid, furfural, and formic acid from lignocellulose on a commercial scale.

The details of one or more embodiments of the invention are set forth in the accompanying drawings and the description below. Other features, objects, and advantages of the invention will be apparent from the description and drawings, and from the claims.

In a first aspect, the disclosure provides a method, including: supplying a reactant mixture including cellulose and hemicellulose in a reactor; providing steam to the reactant mixture; condensing a first portion of the steam to heat the reactant mixture; converting at least a portion of the cellulose to levulinic acid and formic acid and at least a portion of the hemicellulose into furfural; and removing at least a portion of the furfural from the reactor using a second portion of the steam different from the first portion of the steam.

In some embodiments, a yield of levulinic acid is at least 44 wt. %. In some embodiments, a yield of levulinic acid is at least 50 wt. %.

In some embodiments, a yield of formic acid is at least 20 wt. %.

In some embodiments, a yield of furfural is at least 45 wt. %. In some embodiments, a yield of furfural is at least 50 wt. %.

In some embodiments, the method further includes removing at least a portion of the formic acid from the reactor using the second portion of the steam.

In some embodiments, the furfural is removed by the second portion of the steam using steam stripping.

In some embodiments, an amount of steam provided to the reactant mixture corresponds to an amount of steam calculated to heat the reactant mixture to a target temperature as well as an additional amount of steam calculated to reduce an amount of furfural in the reactant mixture below a target concentration of furfural. In some embodiments, the target concentration of furfural is 0.35 wt. % in the reactant mixture. In some embodiments, the target temperature is from of 190° C. to 205° C.

In some embodiments, the reactor includes a back-pressure control valve; removing at least a portion of the furfural using a second portion of the steam forms a vapor stream including steam and furfural; and the stream passes through the back-pressure control valve. In some embodiments, at a fixed steam supply rate, a flow rate of the steam through the back-pressure control valve controls and a pressure of the reactor and a temperature of the reactor.

In some embodiments, an amount of steam provided to the reactant mixture corresponds to an amount of steam calculated to heat the reactant mixture to a target temperature as well as an additional 25% to 100% of the amount of steam calculated to heat the reactor to the target temperature, and the additional 25% to 100% of the amount of steam calculated to heat the reactor to the target temperature corresponds to the second portion of the steam. In some embodiments, the target temperature is from of 190° C. to 205° C.

In some embodiments, an amount of the second portion of the steam is from 5.6 to 28 wt./wt. ratio of a total reactor feed. In some embodiments, the steam stripping rate is selected to provide a stripping factor of from 0.25 to 1.75.

In some embodiments, the method further includes, while providing the steam, contacting the reactant mixture with a mineral acid catalyst.

In some embodiments, the reactor is heated to a temperature of 190° C. to 205° C.

In some embodiments, the reactor is at thermodynamic equilibrium.

In some embodiments, an agitation rate in the reactor is 60 rpm to 100 rpm.

In some embodiments, the steam agitates the reactant mixture.

In some embodiments, the reactant mixture includes lignocellulose, wood, wood pulp, forestry trimmings, paper, corrugated cardboard, sawdust, paper pulp, agricultural residues, food processing waste and/or kelp.

DESCRIPTION OF DRAWINGS

Like reference symbols in the various drawings indicate like elements.

DETAILED DESCRIPTION

Figure 1:
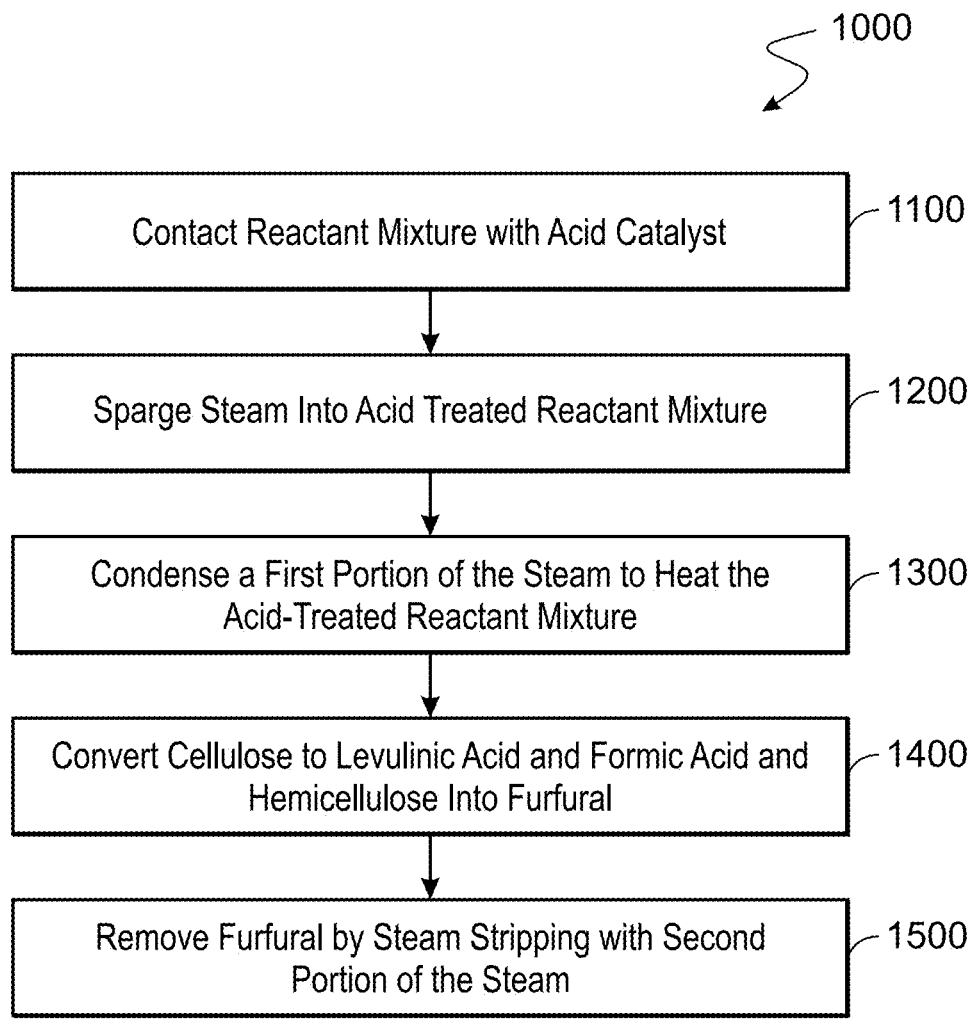
FIG. 1 is a schematic for a method for producing levulinic acid, furfural, and formic acid.

FIG. 1 is a schematic for a method 1000 for producing levulinic acid, furfural, and formic acid.

In step 1100, a reactant mixture that includes cellulose and hemicellulose is contacted with a mineral acid catalyst. The reactant mixture can include a cellulosic feedstock such as lignocellulose (woody materials), wood, wood pulp, forestry trimmings, waste paper, corrugated cardboard, sawdust, paper pulp, agricultural residues, food processing waste and/or kelp. Examples of the mineral acid used in the acid hydrolysis include a mineral acid such as sulfuric acid, nitric acid, hydrochloric acid, hydrobromic acid, and p-toluene sulfonic acid. In some embodiments, the concentration of mineral acid after contacting with the reaction mixture is at least 2 (e.g., at least 2.5, at least 3, at least 3.5, at least 4, at least 4.5, at least 5, at least 5.5, at least 6, at least 6.5, at least 7, at least 7.5, at least 8, at least 8.5, at least 9, at least 9.5) wt. % and/or at most 10 (e.g., at most 9.5, at most 9, at most 8.5, at most 8, at most 7.5, at most 7, at most 6.5, at most 6, at most 5.5, at most 5, at most 4.5, at most 4, at most 3.5, at most 3, at most 2.5) wt. %.

In step 1200, steam is sparged into the acid-treated reactant mixture. In some embodiments, the steam can include a chemical inhibitor, such as a corrosion inhibitor.

In step 1300, a first portion of the steam is condensed to heat the acid-treated reactant mixture. A second portion of the steam different from the first portion of the steam does not condense under the reaction conditions and is used for steam stripping (see discussion below).

In step 1400, at least a portion of the cellulose is converted into levulinic acid and formic acid and at least a portion of the hemicellulose is converted into furfural. Without wishing to be bound by theory, it is believed that the conversion in the step 1400 occurs due to the heating from the step 1300 and the catalytic effect of the mineral acid.

In step 1500, at least a portion of the furfural is removed from the other compounds in the reaction mixture (the mineral acid, the water, the unreacted reactants, the levulinic acid, and/or the formic acid) by steam stripping using the second portion of the steam. In some embodiments, at least a portion of the formic acid may also be removed by the steam stripping. In some embodiments the concentration of furfural in the reactor liquid after removal by steam stripping is reduced to at most 0.35 (e.g., at most 0.3, at most 0.28, at most 0.25, at most 0.2) wt. %. In some embodiments, the concentration of formic acid in the reactor liquid after removal by steam stepping is reduced to at most 0.85 (e.g., at most 0.8, at most 0.75, at most 0.7, at most 0.65, at most 0.6, at most 0.55, at most 0.5) wt. %.

Without wishing to be bound by theory, it is believed that in the reactor, furfural can form resins and/or tar, which can deposit on the reactor surfaces, causing reactor fouling. Additionally, the presence of furfural in the reactor liquid can complicate downstream processing. Thus, removal of furfural in the step 1500 by steam stripping can reduce the presence of resins and/or tar, reduce reactor fouling, and/or facilitate downstream processing. Therefore, it is desirable to minimize the concentration of furfural in the reactor liquid. Without wishing to be bound by theory, it is believed that it can be desirable to maintain the concentration of furfural in the reaction liquid below 0.35 wt. % (0.00066 mole fraction) (see discussion below).

The steps 1200, 1300, 1400, and 1500 are performed continuously and simultaneously in a single reaction vessel (see discussion below).

Without wishing to be bound by theory, it is believed that furfural and formic acid are temperature sensitive and can degrade and/or form resins if exposed to elevated temperatures for prolonged periods of time. Heating using steam allows for greater control of the temperature in the reactor (particularly the temperature of the reactor wall) and/or more uniform heating relative to certain other methods for heating, such as heating using an electric heating mantle. Additionally, removal of furfural and formic acid by steam stripping from the reactor liquid reduces the exposure time to the elevated temperatures in the reactor. Thus, the method 1000, which includes steam for both heating and stripping, can provide higher yields of furfural and/or formic acid relative to certain other methods, such as methods that include an electric heating mantle.

The levulinic acid, furfural, and/or formic acid produced in the method 1000 can be converted into biofuels, fuel additives, commodity chemicals, chemical intermediates, and/or specialty chemicals for use in pharmaceuticals and other consumer products. The levulinic acid and/or other products can undergo further processing before use. For example, a hydrolysate containing levulinic acid, and optionally formic acid, can be concentrated (e.g., by vacuum evaporation) to a syrup containing levulinic acid and formic acid, if present. Levulinic acid in the syrup can be extracted using a suitable solvent (e.g., methyl tetrahydrofuran) and esterified with ethanol to produce ethyl levulinate, hydrogenated to produce gamma valerolactone, and/or oxidized to produce succinic acid or 3-hydroxypropionic acid.

The method 1000 provides relatively high yields of the levulinic acid, furfural, and formic acid. In some embodiments, the yield of levulinic acid is at least 44 (e.g., at least 45, at least 46, at least 47, at least 48, at least 49, at least 50, at least 51, at least 52, at least 53, at least 54, at least 55, at least 56) wt. % and/or at most 57 (e.g., at most 56, at most 55, at most 54, at most 53, at most 52, at most 51, at most 50, at most 49, at most 48, at most 47, at most 46, at most 45) wt. % from cellulose. In some embodiments, the yield of formic acid is at least 20 (e.g., at least 21) wt. % and/or at most 22 (e.g., at most 21) wt. % from cellulose. In some embodiments, the yield of furfural is at least 50 (e.g. at least 51, at least 52, at least 53, at least 54, at least 55, at least 56, at least 57, at least 58, at least 59) wt. % and/or at most 60 (e.g., at most 59, at most 58, at most 57, at most 56, at most 55, at most 54, at most 53, at most 52, at most 51) wt. % from hemicellulose.

In some embodiments, the yield of levulinic acid is at least 44 wt. % from cellulose.

In some embodiments, the yield of levulinic acid is at least 50 wt. % from cellulose.

In some embodiments, the yield of levulinic acid is at least 56 wt. % from cellulose.

In some embodiments, the yield of levulinic acid is 57 wt. % from cellulose.

The yield of levulinic acid and formic acid are defined as the mass of levulinic acid or formic acid produced divided by the mass of cellulose in the reactant mixture. Similarly, the yield of furfural is defined as the mass of furfural produced divided by the mass of hemicellulose in the reactant mixture.

Figure 2:
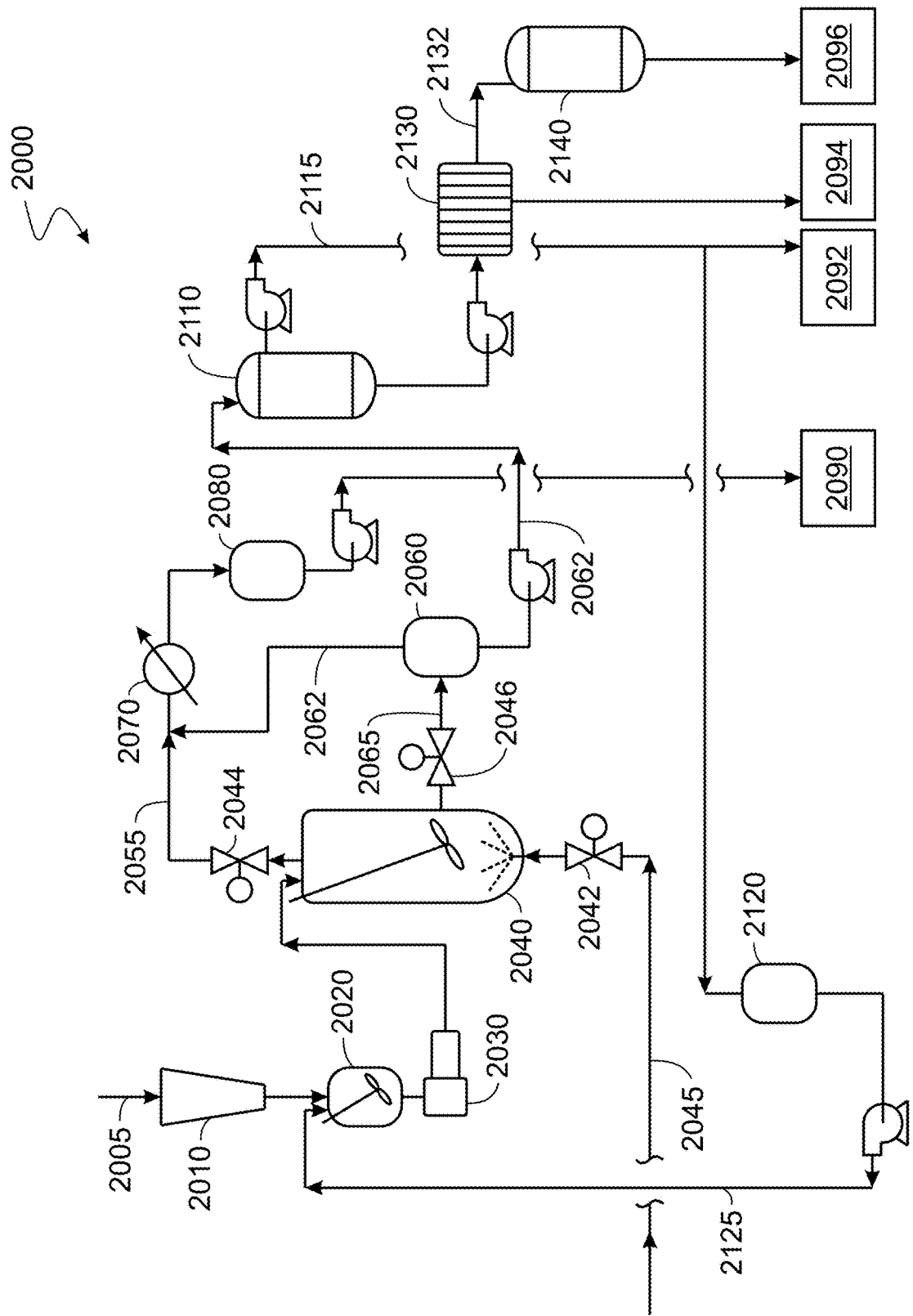
FIG. 2 depicts a schematic of a system 2000 for producing levulinic acid, furfural, and formic acid.

FIG. 2 depicts a schematic of a system 2000 for producing levulinic acid, furfural, and formic acid using the method 1000.

A feedstock 2005 including cellulose and hemicellulose is ground and metered via a solids volume feeder 2010 into an agitated mixing vessel 2020. The feedstock 2005 can also include lignin and/or ash. The feedstock can include a cellulosic feedstock such as lignocellulose (woody materials), wood, wood pulp, forestry trimmings, paper, corrugated cardboard, sawdust, paper pulp, agricultural residues, food processing waste, and/or kelp. In some embodiments, the feedstock is ground to an average particle size of at least 0.1 cm (e.g., at least 0.15, at least 0.2, at least 0.25, at least 0.3, at least 0.35, at least 0.4, at least 0.45) and/or at most 0.5

(e.g., at most 0.45, at most 0.4, at most 0.35, at most 0.3, at most 0.25, at most 0.2, at most 0.15) cm.

In the mixing vessel 2020, the feedstock 2005 is mixed with dilute aqueous acid catalyst (e.g., sulfuric acid). The acid catalyst can be recycled at a controlled flowrate (see discussion below). From the mixing vessel 2020, the acid-treated feedstock is fed by a progressing cavity pump 2030 into a reactor 2040. In some embodiments, the acid-treated feedstock is fed by the progressing cavity pump 2030 at a slurry consistency of at least 5 (e.g., at least 6, at least 7, at least 8, at least 9, at least 10, at least 11, at least 12, at least 13, at least 14, at least 15, at least 16, at least 17, at least 18, at least 19) wt. % and/or at most 20 (e.g., at most 19, at most 18, at most 17, at most 16, at most 15, at most 14, at most 13, at most 12, at most 11, at most 10, at most 9, at most 8, at most 7, at most 6) wt. %. In some embodiments, the temperature of the acid-treated feedstock fed into the reactor 2040 is at least 25 (e.g., at least 50, at least 75° C.) and/or at most 100 (e.g., at most 75, at most 50° C.) In some embodiments, the acid-treated feedstock is fed by the progressing cavity pump 2030 at an average feed rate of 410 (e.g., at least 450) kg/hour to 475 (e.g., at most 450) kg/hour. The reactor 2040 is mechanically agitated and sparged with steam 2045 to maintain the temperature in the reactor 2040 at a desired temperature (see discussion below). Without wishing to be bound by theory, it is believed that temperatures above 200° C. (beyond a limited exposure time) can cause the degradation of formic acid and/or furfural. In general, the steam 2045 can be produced using any suitable method, such as in a separate boiler, for example at a pressure of 17 barg to 24 barg. In general, the steam supplied to the reactor 2040 is from a higher pressure source than the reactor 2040.

The steam sparging rate is the total amount of steam input into the reactor 2040 and includes both the steam used for heating and the steam used for stripping. The steam used to heat the reactor 2040 to the desired temperature (by condensation) is calculated, and additional steam for stripping is provided (see discussion below). The desired total flowrate of steam input into the reactor 2040 can be controlled using the steam flow control valve 2042. The amount of steam 2045 used to maintain the reactor 2040 at the desired temperature is calculated by enthalpy balance. The steam 2045 input into the reactor 2040 also includes excess steam beyond the steam that condenses (see discussion below). This portion of the steam flows through the reactor 2040 as a separate phase at the same temperature as the reactor 2040 and does not condense or contribute significantly to heating the reactor 2040 and exits the reactor 2040 through a back-pressure control valve 2044 as a stream 2055 and acts as stripping steam. Without wishing to be bound by theory, it is believed that the stripping steam provides a separate portion of the reactor to which furfural can migrate as soon as it is formed and be carried out along with the stream 2055. A portion of the formic acid produced in the reaction can also leave in the stream 2055. Thus, the concentrations of furfural and formic acid in the reactor 2040 can be continuously maintained at relatively low levels.

Without wishing to be bound by theory, it is believed that the steam that does not condense can also provide agitation to supplement the agitation provided by the mechanical agitator. It is further believed that this reduces the power input used for other agitation methods and maintains the vapor bubbles as a separate phase. It is also believed that the stripping steam leaving the reactor 2040 also provides a substantial vapor flow through the back-pressure control valve 2044, allowing for relatively stable reactor pressure control using the back-pressure control valve 2044. Stable control of the reactor pressure determines the reactor temperature.

The liquid level in the reactor 2040 is monitored via a level control sensor and is controlled by modulating the opening of a outlet valve 2046 controlled by the level control sensor. The residence time of the liquid in the reactor 2040, which can include levulinic acid, unreacted starting material, unused mineral acid, residual furfural, residual formic acid, and/or water is determined by setting the level control sensor to maintain a desired volume in the reactor. The residence time is then the ratio of set volume to volumetric feed rate set by the progressing cavity pump 2030 and the steam condensing rate. In some embodiments, the set point for the level controller is set to at least 40 (e.g., at least 45, at least 50, at least 55, at least 60, at least 65, at least 70) % and/or at most 75 (e.g., at most 70, at most 65, at most 60, at most 55, at most 50) % of the total volume of the reactor 2040. In some embodiments, the residence time in the reactor 2040 is at least 30 (e.g., at least 35, at least 40, at least 45, at least 50, at least 55) minutes and/or at most 60 (e.g., at most 55, at most 50, at most 45, at most 40, at most 35) minutes. Without wishing to be bound by theory, it is believed that extension of the reactor time beyond 60 minutes does not significantly affect yields. It is further believed that to accommodate longer reaction times, a larger reactor would be employed, potentially increasing costs. Additionally, longer reactor times may also increase degradation of reactants and/or products and fouling of internal surfaces of the reactor 2040 by resin and/or tar deposition.

The steam flow control valve 2042 provides control of the steam flow, the back-pressure control valve 2044 provides pressure and temperature control of the reactor 2040, and the liquid outlet valve 2046 provides level control of the reactor 2040.

In some embodiments, the liquid phase residence time in the reactor 2040 is at least 30 (e.g., at least 35, at least 40) minutes and/or at most 45 (e.g., at most 40, at most 35) minutes. In general, the liquid phase residence time can be controlled by the level control sensor and the liquid outlet valve 2046.

A stream 2065, which is a mixture of liquid and vapor and can include levulinic acid, unreacted starting material, unused mineral acid, residual furfural, formic acid, and/or water, leaves the reactor 2040 through the liquid outlet valve 2046 and flows into the flash tank 2060. The flash tank 2060 is maintained at around atmospheric pressure. In the flash tank 2060 the superheated liquid from the stream 2065 flashes and cools producing 15 to 40% of its mass as vapor. The vapor and liquid in the flash tank 2060 separate by gravity. A vapor stream 2062 containing furfural and formic acid exits the flash tank 2060 and is combined with the stream 2055 from the back-pressure control valve 2044 and the combined vapor streams are condensed in a condenser 2070 and collected in a tank 2080. The tank 2080 is periodically emptied into collection totes 2090 for storage and subsequent weighing and analysis.

A liquid stream 2064 containing levulinic acid and formic acid exits the flash tank 2060 and is pumped to and collected in a tank 2110 where biochar created in the hydrolysis reaction is allowed to settle out. In some embodiments, the biochar is separated out by filtration. A stream 2115 of clarified, supernatant liquid containing the acid catalyst from the tank 2110 is pumped to a tank 2120 (or to collection totes 2092) and then pumped back to the mixing vessel 2020 to be mixed with incoming feedstock. The conductivity of the recycled acid hydrolysate in the tank 2120 is measured and used to control the addition of supplemental acid catalyst. To recycle the acid catalyst, a stream 2125 containing the acid catalyst can be taken from the tank 2120 and added to the mixing vessel 2020. Settled biochar from the tank 2110 is filtered in a filter 2130 to remove the solid biochar. Solid biochar from the filter 2130 is collected and stored for subsequent analysis in the collection tote 2094. Filtrate liquid 2132 from the filter 2130 is collected in a tank 2140 and from there it is pumped to collection tote 2096 where it is stored for subsequent analysis. At the end of an operation, liquids in the mixing vessel 2020, the flash tank 2060, the tank 2080, the tank 2110, the tank 2120, the tank 2140, the reactor 2040, the totes 2090, 2092, 2094, and 2096, and in the separated biochar solids can be weighed, sampled, and analyzed for levulinic acid, formic acid, and furfural to determine the total amounts of products in the system 2000. Without wishing to be bound by theory, it is believed that typically the locations of the levulinic acid, formic acid, and furfural produced are known due to their volatility. Yields of products can be calculated knowing the mass of feedstock 2005 fed to the reactor 2040, the composition of the feedstock 2005 and the volume of liquid and the concentrations of products in each of the tanks, collection totes and in the liquid in the char cake from the filter 2130.

The reactor 2040 can be operated under stable, continuous operation as steam can continually be added and removed and product can continually be generated and removed without having to halt the process. The reactor 2040 can be operated at steady state. Without wishing to be bound by theory, it is believed that because the heating and stripping are both being conducted using steam, the temperature of the reactor 2040 and the stripping rate can be controlled by the reactor back-pressure using the back-pressure control valve 2044 and the steam addition rate can be controlled using the steam flow control valve 2042, resulting in a relatively smooth and stable operation at the controlled conditions.

In some embodiments, the temperature of the reactor 2040 and the temperature at which the method 1000 is performed is at least 190 (e.g., at least 191, at least 192, at least 193, at least 194, at least 195, at least 196, at least 197, at least 198, at least 199, at least 200, at least 201, at least 202, at least 203, at least 204° C.) and/or at most 205 (e.g., at most 204, at most 203, at most 202, at most 201, at most 200, at most 199, at most 198, at most 197, at most 196, at most 195, at most 194, at most 193, at most 192, at most 191° C.)

The reactor 2040 is continuously maintained at a constant pressure. In some embodiments, the pressure of the reactor 2040 and the pressure at which the method 1000 is performed is at least 11.5 (167 psig) (e.g., at least 12, at least 12.5, at least 13) barg and/or at most 13.5 (e.g., at most 13, at most 12.5, at most 12) barg. In some embodiments, the pressure of the reactor 2040 and the pressure at which the method 1000 is performed is at least 167 (e.g., at least 170, at least 175, at least 180, at least 185, at least 190, at least 195) psig and/or at most 196 (e.g., at most 195, at most 190, at most 185, at most 180, at most 175, at most 170) psig.

The steam stripping corresponds to the excess steam in addition to the steam used for heating. In some embodiments, the excess of steam is at least 25 (e.g., at least 30, at least 35, at least 40, at least 45, at least 50, at least 55, at least 60, at least 65, at least 70, at least 75, at least 80, at least 85, at least 90, at least 95) % and/or at most 100 (e.g., at most 95, at most 90, at most 85, at most 80, at most 75, at most 70, at most 65, at most 60, at most 55, at most 50, at most 45, at most 40, at most 35, at most 30) % more than the amount of steam used to heat the reactor 2040 to the target temperature. Without wishing to be bound by theory, it is believed that continuous steam stripping at these rates achieves almost complete removal of both furfural and formic acid from the reactor liquids relatively rapidly, thereby minimizing exposure of these products to the elevated temperatures and acidity present in the reactor 2040.

In some embodiments, the steam stripping rate is selected to reduce the furfural concentration in the reactor liquid to below a target concentration (e.g., 0.35 wt. %). Without wishing to be bound by theory, it is believed that reducing the furfural concentration to below the target concentration can reduce (e.g., avoid) fouling by furfural-derived tars and resin deposition. Without wishing to be bound by theory, the minimum stripping steam rate to reduce the furfural concentration in the reactor liquid to the desired concentration (e.g., 0.35 wt. %) can be estimated based on the steam stripping factor(S).

Figure 3:
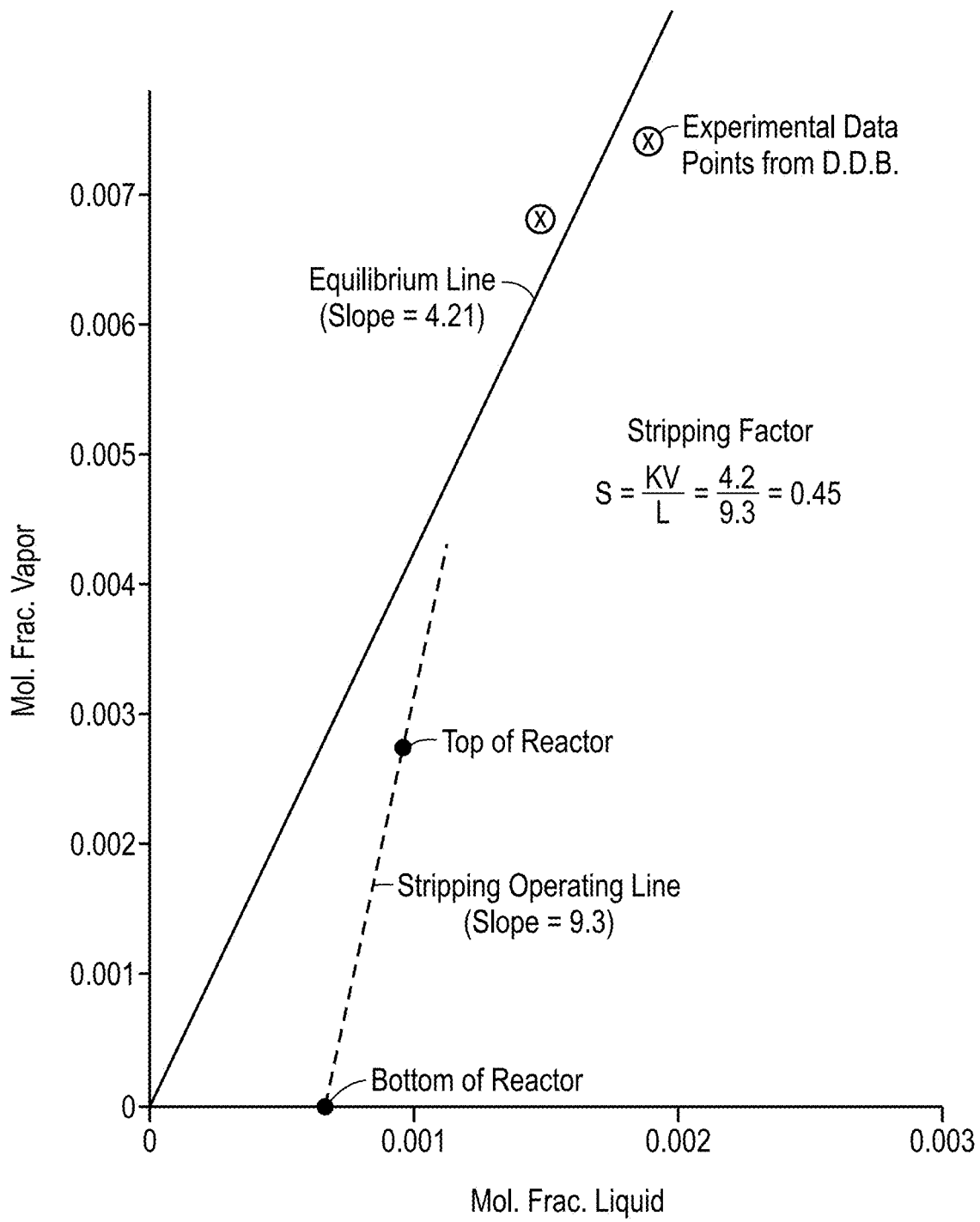
FIG. 3 depicts a graph of a furfural-water vapor-liquid equilibrium line and a reactor-furfural stripping operating line.

The steam stripping factor(S) can be calculated using the ratio of the slopes of the furfural-water vapor-liquid equilibrium line and the stripping operating line, as shown in FIG. 3 and the equation:

$$S = KV/L$$

where $K$ is the slope of the furfural-water equilibrium line (vapor-liquid), and $L/V$ is the slope of the reactor-stripping operating line. The reactor-stripping operating line slope is the ratio of the liquid molar feed flow ($L$), corresponding to the feed rate of the liquid reactant, and the molar steam stripping rate ($V$). The slope of the reactor stripping operating line ($L/V$) is defined as the ratio of the average molar liquid flow ($L$) in kg moles/hr to the stripping steam flow ($V$) in kg moles/hr. For a given system with a fixed equilibrium curve and fixed liquid feed composition, the higher the steam stripping rate the higher the stripping factor. The same stripping factor can be applied regardless of the scale of operation. A sufficiently high stripping factor results in a low furfural concentration in the reactor exit liquid. The furfural equilibrium data at high pressure and dilute concentration (such as that in the reactor 2040) can be taken from published data (e.g., Dortmund Data Bank).

The slope of the reactor operating line is determined based on the desired limiting furfural concentration in the reactor liquid and the concentration of furfural in the reactor feed slurry (recycled furfural plus potential furfural as hemicellulose). The operating line connects the two points shown in FIG. 3, representing conditions at either end of the reactor. At one end is the desired limiting liquid furfural concentration (0.35 wt. % or 0.00066 mole fraction) and the stripping steam (furfural concentration=0). At the other end, the feed liquid furfural concentration including the potential furfural in the hemicellulose and the furfural concentration in the exiting vapor in equilibrium with the limiting furfural concentration in the liquid (see Example below).

In some embodiments, a target steam stripping factor is selected and the steam stripping rate is set to achieve the target steam stripping factor. In some embodiments, the steam stripping factor is at least 0.25 (e.g., at least 0.5, at least 0.75, at least 1, at least 1.25, at least 1.5) and/or at most 1.75 (e.g., at most 1.5, at most 1.25, at most 1, at most 0.75, at most 0.5). The amount of steam to heat the reactor 2040 is then calculated and the steam sparging rate, corresponding to the sum of the steam stripping rate and the steam used for heating, is set by adjusting the steam flow control valve 2042.

In some embodiments, the stripping factor is at least 0.25 (e.g., at least 0.3, at least 0.35, at least 0.4, at least 0.45, at least 0.5, at least 0.55, at least 0.6, at least 0.65, at least 0.7, at least 0.75, at least 0.8, at least 0.85, at least 0.9, at least 0.95, at least 1, at least 1.05, at least 1.1, at least 1.15, at least 1.2, at least 1.25, at least 1.3, at least 1.35, at least 1.4, at least 1.45, at least 1.5, at least 1.55, at least 1.6, at least 1.65, at least 1.7) and/or at most 1.75 (e.g., at most 1.7, at most 1.65, at one most 1.6, at most 1.55, at most 1.5, at most 1.45, at most 1.4, at most 1.35, at most 1.3, at most 1.25, at most 1.2, at most 1.15, at most 1.1, at most 1.05, at most 1, at most 0.95, at most 0.9, at most 0.85, at most 0.8, at most 0.75, at most 0.7, at most 0.65, at most 0.6, at most 0.55, at most 0.5, at most 0.45, at most 0.4, at most 0.35, at most 0.3) for the furfural-water system. In some embodiments, the steam stripping rate is at least 31.5 (e.g., at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155) kg/hour and/or at most 157.5 (e.g., at most 155, at most 150, at most 145, at most 140, at most 135, at most 130, at most 125, at most 120, at most 115, at most 110, at most 105, at most 100, at most 95, at most 90, at most 85, at most 80, at most 75, at most 70, at most 65, at most 60, at most 55, at most 50, at most 45, at most 40, and most 35) kg/hour. In some embodiments, an amount of the stripping steam is at least 5.6 (e.g., at least 10, at least 15, at least 20, at least 25) and/or 28 (e.g., at most 25, at most 20, at most 15, at most 10) wt./wt. ratio of the total reactor feed.

Without wishing to be bound by theory, it is believed that the temperature and pressure of the reactor 2040 can be controlled by controlling the amount of steam vapor exiting the reactor 2040 via the back-pressure control valve 2044. As discussed above, the amount of steam used to maintain the reactor at the desired temperature is calculated by enthalpy balance and the desired level of additional stripping steam in addition to the heating steam is calculated from the stripping factor as described above. The stripping steam passes through the reactor 2040 and is throttled by the back-pressure control valve 2044, which is set to control the pressure of the reactor 2040 at that used to control the reactor 2040 at the desired temperature. Without wishing to be bound by theory, it is believed that when the temperature, pressure and chemical potential of the liquid and the vapor in the reactor 2040 are equal, the reactor 2040 is at stable thermodynamic equilibrium (steady state). When the liquid feed rate and the steam feed rate are fixed, the temperature of the reactor 2040 can then be controlled at steady state by adjustment of the back pressure provided by the back-pressure control valve 2044. The chemical potential is the tendency of a volatile component such as furfural or water to transfer between liquid and vapor. In the reactor 2040 at equilibrium, the amount of furfural leaving with the stripping steam (in the stream 2055) is in equilibrium with the amount of furfural remaining in the liquid. It is further believed that controlling the conditions of the reactor 2040 can prevent degradation of the products due to excessive exposure to fluctuating elevated temperatures in the reactor 2040. Without wishing to be bound by theory, it is believed that the method 1000 and the reactor 2040 can be operated under relatively steady state controlled conditions, thereby allowing for a predictable scalability.

The reactor 2040 can be subject to continuous, moderate agitation. In some embodiments, the agitation rate is at least 60 (e.g., at least 65, at least 70, at least 75, at least 80, at least 85, at least 90, at least 95) rpm and/or at most 100 (e.g., at most 95, at most 90, at most 85, at most 80, at most 75, at most 70, at most 65) rpm. Without wishing to be bound by theory, it is believed that the reactor 2040 should be agitated at a rate fast enough to maintain good back-mixing but slow enough to avoid emulsification of the stripping steam with the reaction liquids. It is also believed that the stripping steam residence time and flow path through the reaction zone are controlled by the agitation rate of the reactor 2040. It is further believed that back-mixing due to the moderate agitation is enhanced by turbulence due to the rising bubbles due to non-condensed stripping steam. Additionally, it is believed that a moderate agitation speed (e.g., less than 100 rpm) allows the stripping steam to more easily form a separate non-condensed phase with a direct path through the reactor 2040, thereby allowing a lower stripping steam hold-up time in the reactor 2040, easier migration of the furfural and formic acid to the steam phase and a relatively rapid removal of furfural and formic acid from the reactor 2040.

Without wishing to be bound by theory, it is believed that the yields of levulinic acid, furfural, and/or formic acid in the method 1000 can be negatively impacted by variations due to poor control of the reactor conditions such as the temperature, the pressure, the acid strength, the residence time, the mixing regime, and the reactant concentrations of the reactor 2040.

Without wishing to be bound by theory, it is believed that the temperature determines the rate of both desirable and undesirable parallel reactions. Temperature excursions above the desired level can lead to waste biochar production, reactor fouling, and loss of yield. Temperature excursions below the desired level can lead to incomplete reaction, loss of reactor productivity, and consequent reduced yields.

Without wishing to be bound by theory, it is believed that the reactor pressure, determined by the back-pressure provided by the back-pressure control valve 2044, also determines the temperature. Because the reactor vapor is in equilibrium with the liquid, control of the reactor vapor back-pressure is a convenient method of controlling the reactor temperature.

Without wishing to be bound by theory, it is believed that the acid is the reaction catalyst and its concentration determines the rate of both desirable and undesirable parallel reactions. Excursions of acid concentration above the desired set point leads to excessive reactor fouling due to resin and tar deposition and reactor corrosion. Excursions below the desired set point leads to loss of conversion, loss of yield, and lower reactor productivity.

Without wishing to be bound by theory, it is believed that the reactor residence time determines the extent to which reactions in the reactor reach completion. Too long a residence time can lead to product degradation, reactor fouling due to tar and resin deposition and loss of reactor productivity. Too short a residence time can result in incomplete conversion and loss of yields of the desired products.

Without wishing to be bound by theory, it is believed that the mixing regime determines how selective the reactor conditions are in favor of the desirable reactions to form levulinic acid, formic acid, and furfural compared with biochar resins. It is believed that reactor liquid that is fully back-mixed favors the lower order over the higher order chemical reactions producing levulinic and formic acid rather than waste biochars (or humins). It is further believed that the stripping steam vapor flows through the reactor essentially in non-back-mixed "plug flow" mode that favors production of furfural from hemicellulose over waste biochar (or humins).

Without wishing to be bound by theory, it is believed that variation of reactant (cellulose and hemicellulose) concentration can lead to over-production of biochar waste if present at too high a level or loss of reaction if present at too low a level.

Without wishing to be bound by theory, it is believed that variation of reactor conditions such as absence of stripping steam can lead to longer than desired residence times for furfural and formic acid and therefore undesirable conversion of furfural to waste biochar (or humins) and degradation of formic acid to carbon monoxide. These reactions would result in lower yields of furfural and formic acid.

Without wishing to be bound by theory, it is believed that variation of reactor conditions such as too low a heating steam flow can lead to poor control over reactor temperature and consequent loss of reactor productivity and/or reactor fouling due to internal deposition of tars and resins. Without wishing to be bound by theory, it is believed that variation of reactor conditions, such as too low or no stripping steam flow exiting via the pressure control valve, can lead to poor control over reactor pressure and consequent loss of reactor temperature control, thereby reducing reactor productivity and/or causing reactor fouling due to internal deposition of tars and resins.

Example

A single stage reactor (part of a pilot plant) was operated to convert a mixed lignocellulosic waste into levulinic acid, formic acid, and furfural by dilute acid hydrolysis at elevated temperature. The process setup corresponds to the system 2000 shown in FIG. 2. The overall continuous hydrolysis plant operation lasted 60.5 hours and operation with feedstock was maintained for 55.5 hours. Plant operation was stable after warm-up (5 hours) and during feeding (55.5 hours).

The feedstock used was mixed post-consumer waste fiber. The quantity of waste lignocellulose fed during the operation was 827.7 kg (dry basis). The feedstock composition on a dry basis (moisture-free) was analyzed as 58.26 wt. % cellulose, 15.77 wt. % hemicellulose, 22.79 wt. % lignin, and the balance (3.2 wt. %) being inorganic ash. The masses of cellulose and hemicellulose fed were therefore 482.23 kg and 130.53 kg, respectively. This represents a typical lignocellulosic feedstock composition although other lignocellulosic feedstocks can be used. The feedstock was ground to an average particle size of around 5 mm. The average feed rate of lignocellulose was 14.9 kg/h.

It was desired to maintain the furfural level below 0.35 wt. % to prevent its degradation to waste biochar and to maintain the formic acid level as low as possible. At one end of the reactor, the desired limiting liquid furfural concentration was 0.00066 mole fraction and the stripping steam had a furfural concentration of 0 and, at the other end, the feed liquid furfural concentration including the potential furfural in the hemicellulose was 0.00096 mole fraction and the furfural concentration in the exiting vapor in equilibrium with the limiting furfural concentration in the liquid was 0.0028 mole fraction. These two points provide a slope of L/V of 9.3 (FIG. 3). The slope of the equilibrium line (K) for furfural and water at a pressure of 10 bar is 4.21 (Dortmund Data Bank). The steam stripping factor determined to maintain the furfural concentration at the desired concentration was calculated as 4.21/9.3=0.45. The minimum steam stripping rate (V) to reduce the furfural concentration to 0.35 wt. % is therefore V=S*L/K=0.45*24.3/4.21=2.6 kg moles/hour or 46.8 kg/hour.

A steam feed of 151 kg/hour was calculated, by enthalpy balance, to provide sufficient steam to condense into the reactor to maintain the reactor at 193° C. The steam input into the reactor also included an additional 49 kg/hour (24.5%) excess steam beyond the steam that condenses, corresponding to 5% above the minimum of 46.8 kg/hour. Thus, the total steam sparging rate was 200 kg/hour.

The set point for the level controller was set at 57% of the total reactor volume. The reactor residence time was about 45 minutes.

HPLC analyses were initially carried out at the pilot plant laboratory. Analyses of some of the samples were also verified by replication in a separate independent laboratory.

Recording of the volume collected in each of the process tanks along with the HPLC analyses of representative samples from the tanks resulted in calculation of the total quantity of levulinic acid, formic acid and furfural produced by the end of the operation. These quantities were 210.6 kg levulinic acid, 97.45 kg formic acid, and 64.67 kg furfural. The yields were therefore calculated as 44 mass % (61 mol. %) levulinic acid (on cellulose), 20 mass % (71 mol. %) formic acid (on cellulose) and 50 mass % (68 mol. %) furfural (on hemicellulose).

Surprisingly, all three products were obtained together at yields equal to or higher than previously reported. This was unexpected as only a single reactor vessel was used, the reactor residence time was 45 minute,s and the steam stripping rate to remove furfural was as low as 8.7% of the total reactor feed liquid including condensing steam (561 kg/hour). The concentration of furfural measured in the liquid in R-102 and in the flash tank 2060 was maintained at 0.28 wt. %, which was below the desired minimum of 0.35 wt. %. The percentage of furfural recovered via the steam stripping was 76% of that produced based on the measured furfural in the total condensate plus that remaining in the tank 2080 divided by the total output of furfural. Without wishing to be bound by theory, it is believed that the high simultaneous yields of levulinic acid, formic acid, and furfural obtained and the low stripping rate of steam to remove furfural are due to a several factors constituting the conditions of operation of the reactor discussed above. A summary of the feedstock and final tank quantities of products is shown in Table 1 and Table 2, respectively.

TABLE 1

Summary of the feedstock

| | |
|---|---|
| Feedstock (dry basis) | 827.72 kg |
| Cellulose | 482.23 kg |
| Hemicellulose | 130.53 kg |
| Lignin | 188.64 kg |
| Ash | 26.32 kg |

TABLE 2

Final tank quantities of products in tanks and collection totes

| | Volume (L) | Levulinic acid (kg) | Formic acid (kg) | Furfural (kg) |
|---|---|---|---|---|
| Mixing vessel 2020 | 339.2 | 9.77 | 0.0 | 0.94 |
| Reactor 2040 | 416.4 | 11.74 | 3.55 | 1.18 |
| Flash tank 2060 | 71.5 | 2.37 | 0.68 | 0.24 |
| Tank 2110 | 3194.8 | 89.81 | 35.48 | 6.69 |
| Tank 2120 | 579 | 14.10 | 2.84 | 0.00 |
| Tank 2140 | 1442.2 | 34.36 | 12.24 | 2.87 |
| Tank 2080 | 116.5 | 0.06 | 0.75 | 1.13 |

TABLE 2-continued

Final tank quantities of products in tanks and collection totes

|  | Volume (L) | Levulinic acid (kg) | Formic acid (kg) | Furfural (kg) |
| --- | --- | --- | --- | --- |
| Tote 2092 | 805 | 20.88 | 9.10 | 2.49 |
| Tote 2094 | 905 | 12.57 | 5.00 | 0.00 |
| Tote 2090 | 5837.6 | 2.14 | 22.73 | 48.17 |
| Biochar filtrate liquids 2096 | 455.8 | 12.81 | 5.07 | 0.95 |
| TOTALS |  | 210.61 | 97.45 | 64.66 |

A number of embodiments of the invention have been described. Nevertheless, it will be understood that various modifications may be made without departing from the spirit and scope of the invention. Accordingly, other embodiments are within the scope of the following claims.

What is claimed is:

1. A method, comprising:
   supplying a reactant mixture comprising a feedstock comprising cellulose and hemicellulose, and 2 wt. % to 10 wt. % of a mineral acid catalyst in a reactor;
   providing steam to the reactant mixture;
   condensing a first portion of the steam to heat the reactant mixture;
   converting at least a portion of the cellulose to levulinic acid and formic acid and at least a portion of the hemicellulose into furfural; and
   removing at least a portion of the furfural from the reactor using a second portion of the steam different from the first portion of the steam by steam stripping;
   wherein:
   the feedstock comprises a member selected from the group consisting of lignocellulose, wood, wood pulp, forestry trimmings, paper, corrugated cardboard, sawdust, paper pulp, agricultural residues, food processing waste, and kelp;
   a liquid phase residence time in the reactor is 30 minutes to 60 minutes;
   an amount of steam provided to the reactant mixture corresponds to an amount of steam calculated to heat the reactant mixture to a temperature of 190° C. to 205° C. as well as an additional amount of steam calculated to reduce an amount of furfural in the reactant mixture below 0.35 wt. %;
   a steam stripping rate is selected to provide a stripping factor of from 0.25 to 1.75;
   the reactor comprises a back-pressure control valve;
   removing at least a portion of the furfural using a second portion of the steam forms a vapor stream comprising steam and furfural;
   the vapor stream passes through the back-pressure control valve; and
   at a fixed steam supply rate, a flow rate of the vapor stream through the back-pressure control valve controls a pressure of the reactor and a temperature of the reactor.

2. The method of claim 1, wherein a yield of levulinic acid is at least 44 wt. %.

3. The method of claim 1, wherein a yield of levulinic acid is at least 50 wt. %.

4. The method of claim 1, wherein a yield of formic acid is at least 20 wt. %.

5. The method of claim 1, wherein a yield of furfural is at least 45 wt. %.

6. The method of claim 1, wherein a yield of furfural is at least 50 wt. %.

7. The method of claim 1, further comprising removing at least a portion of the formic acid from the reactor using the second portion of the steam.

8. The method of claim 1, wherein:
   the amount of steam calculated to reduce the amount of furfural in the reactant mixture to below 0.35 wt. % is 25% to 100% of the amount of steam calculated to heat the reactor.

9. The method of claim 1, wherein an amount of the second portion of the steam is from 5.6 to 28 wt./wt. ratio of a total reactor feed.

10. The method of claim 1, wherein the reactor is at thermodynamic equilibrium.

11. The method of claim 1, wherein an agitation rate in the reactor is 60 rpm to 100 rpm.

12. The method of claim 1, wherein the steam agitates the reactant mixture.

* * * * *